(12) United States Patent
Khamis et al.

(10) Patent No.: US 9,737,388 B2
(45) Date of Patent: Aug. 22, 2017

(54) IMPLANTS, TOOLS, AND METHODS FOR TREATMENT OF PELVIC CONDITIONS

(71) Applicant: AMS Research Corporation, Minnetonka, MN (US)

(72) Inventors: Chaouki A. Khamis, Cupertino, CA (US); Jessica L. Roll, Phoenix, AZ (US); Shiva P. Moosai, New Hope, MN (US)

(*) Notice: Subject to any disclaimer, the term of this patent is extended or adjusted under 35 U.S.C. 154(b) by 24 days.

(21) Appl. No.: 14/807,382

(22) Filed: Jul. 23, 2015

(65) Prior Publication Data

US 2015/0327970 A1 Nov. 19, 2015

Related U.S. Application Data

(63) Continuation of application No. 13/432,624, filed on Mar. 28, 2012, now Pat. No. 9,089,393.

(60) Provisional application No. 61/468,069, filed on Mar. 28, 2011.

(51) Int. Cl.
*A61F 2/00* (2006.01)
*A61B 17/00* (2006.01)

(52) U.S. Cl.
CPC .......... *A61F 2/0004* (2013.01); *A61F 2/0031* (2013.01); *A61F 2/0045* (2013.01); *A61B 2017/00805* (2013.01); *A61F 2220/0008* (2013.01)

(58) Field of Classification Search
CPC ......... A61B 2017/00805; A61F 2/0004; A61F 2/0031; A61F 2/0045; A61F 2/0063; A61F 2002/0072

USPC .............................. 600/29–31, 37
See application file for complete search history.

(56) References Cited

U.S. PATENT DOCUMENTS

| | | | |
|---|---|---|---|
| 2,738,790 | A | 3/1956 | Todt et al. |
| 3,124,136 | A | 3/1964 | Usher |
| 3,182,662 | A | 5/1965 | Shirodkar |
| 3,311,110 | A | 3/1967 | Singerman et al. |

(Continued)

FOREIGN PATENT DOCUMENTS

| | | |
|---|---|---|
| AU | 2002241673 | 11/2005 |
| CA | 2404459 | 8/2005 |

(Continued)

OTHER PUBLICATIONS

"Access Instrument System with AlloSling Fascia" (6 pages with two pages of Instructions for Use).

(Continued)

*Primary Examiner* — Christine H Matthews
*Assistant Examiner* — Kaylee Wilson
(74) *Attorney, Agent, or Firm* — Brake Hughes Bellermann LLP

(57) ABSTRACT

Described are various embodiments of surgical procedures, systems, implants, devices, tools, and methods, useful for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the devices and tools including devices and tools for anchoring an implant to supportive tissue and adjusting the implant.

13 Claims, 6 Drawing Sheets

(56) References Cited

U.S. PATENT DOCUMENTS

| | | |
|---|---|---|
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,815,576 A | 6/1974 | Balaban |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,474,518 A | 12/1995 | Velazquez |
| 5,474,543 A | 12/1995 | McKay |
| 5,518,504 A | 5/1996 | Polyak |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,633,286 A | 5/1997 | Chen |
| 5,643,320 A | 7/1997 | Lower et al. |
| 5,669,935 A | 9/1997 | Rosenman et al. |
| 5,683,349 A | 11/1997 | Makower et al. |
| 5,697,931 A | 12/1997 | Thompson |
| 5,709,708 A | 1/1998 | Thal |
| 5,725,541 A | 3/1998 | Anspach, III et al. |
| 5,741,282 A | 4/1998 | Anspach, III et al. |
| 5,782,916 A | 7/1998 | Pintauro et al. |
| 5,785,640 A | 7/1998 | Kresch et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,925,047 A | 7/1999 | Errico et al. |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,010,447 A | 1/2000 | Kardjian |
| 6,027,523 A | 2/2000 | Schmieding |
| 6,030,393 A | 2/2000 | Corlew |
| 6,031,148 A | 2/2000 | Hayes et al. |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,110,101 A | 8/2000 | Tihon et al. |
| 6,117,067 A | 9/2000 | Gil-Vernet |
| 6,127,597 A | 10/2000 | Beyar et al. |
| 6,168,611 B1 | 1/2001 | Rizvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van de Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,414,179 B1 | 7/2002 | Banville |
| 6,423,080 B1 | 7/2002 | Gellman et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,494,906 B1 | 12/2002 | Owens |
| 6,502,578 B2 | 1/2003 | Raz et al. |
| 6,506,190 B1 | 1/2003 | Walshe |
| 6,530,943 B1 | 3/2003 | Hoepffner et al. |
| 6,575,897 B1 | 6/2003 | Ory |

(56) References Cited

U.S. PATENT DOCUMENTS

| | | |
|---|---|---|
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,198,597 B2 | 4/2007 | Siegel et al. |
| 7,226,407 B2 | 6/2007 | Kammerer |
| 7,226,408 B2 | 6/2007 | Harari et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,686,759 B2 | 3/2010 | Sater |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,766,926 B2 | 8/2010 | Bosely et al. |
| 7,789,821 B2 | 9/2010 | Browning |
| 8,172,745 B2 | 5/2012 | Rosenblatt |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0036676 A1 | 2/2003 | Scetbon |
| 2003/0045774 A1* | 3/2003 | Staskin .......... A61B 17/3468 600/29 |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2004/0267088 A1 | 12/2004 | Krammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0038451 A1 | 2/2005 | Rao et al. |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0028828 A1 | 2/2006 | Phillips |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0287571 A1 | 12/2006 | Gozzi |
| 2007/0015953 A1 | 1/2007 | MacLean |
| 2007/0078295 A1 | 4/2007 | Landgrebe |
| 2007/0173864 A1 | 7/2007 | Chu |
| 2008/0039678 A1 | 2/2008 | Montpetit et al. |
| 2008/0300607 A1 | 12/2008 | Meade et al. |
| 2009/0005634 A1 | 1/2009 | Rane |
| 2009/0012353 A1 | 1/2009 | Beyer |
| 2009/0171143 A1* | 7/2009 | Chu .................. A61B 17/0401 600/37 |
| 2009/0221868 A1 | 9/2009 | Evans |
| 2009/0240104 A1* | 9/2009 | Ogdahl ............ A61B 17/0401 600/37 |

(56) References Cited

U.S. PATENT DOCUMENTS

| | | | |
|---|---|---|---|
| 2010/0261950 A1 | 10/2010 | Lund | |
| 2010/0298630 A1* | 11/2010 | Wignall | A61B 17/0469 600/37 |
| 2011/0124954 A1 | 5/2011 | Ogdahl et al. | |

FOREIGN PATENT DOCUMENTS

| | | |
|---|---|---|
| DE | 2305815 | 2/1973 |
| DE | 4220283 C2 | 5/1994 |
| DE | 19544162 | 4/1997 |
| DE | 10211360 | 9/2003 |
| DE | 20016866 | 3/2007 |
| EP | 0248544 A1 | 12/1987 |
| EP | 0470308 A1 | 2/1992 |
| EP | 0650703 A1 | 6/1994 |
| EP | 0643945 A2 | 7/1994 |
| EP | 0632999 A1 | 1/1995 |
| EP | 1093758 A1 | 4/2001 |
| EP | 1060714 A3 | 9/2002 |
| EP | 1342450 B1 | 9/2003 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |
| SU | 1225547 A1 | 4/1986 |
| SU | 1342486 A | 10/1987 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02058563 A1 | 8/2002 |
| WO | WO02062237 A1 | 8/2002 |
| WO | WO02069781 | 9/2002 |
| WO | WO02071953 A2 | 9/2002 |
| WO | WO02078552 A1 | 10/2002 |
| WO | WO02089704 A2 | 11/2002 |
| WO | WO03017848 A1 | 3/2003 |
| WO | WO0303778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03068107 A1 | 8/2003 |
| WO | WO03075792 A1 | 9/2003 |
| WO | WO03092546 A2 | 11/2003 |
| WO | WO03096929 A1 | 11/2003 |
| WO | WO2004012626 A1 | 2/2004 |
| WO | WO2004016196 A2 | 2/2004 |
| WO | WO2004017862 A2 | 3/2004 |
| WO | WO2004034912 A1 | 4/2004 |
| WO | WO2005037132 A2 | 4/2005 |
| WO | WO2005079702 A1 | 9/2005 |
| WO | WO2005122954 A1 | 12/2005 |
| WO | WO2006015031 A2 | 2/2006 |
| WO | WO2006108145 A1 | 10/2006 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |

OTHER PUBLICATIONS

"Introducing: AlloSling Fascia The *Natural Choice* for Suburethral Sling Procedures", Advertisement from UroMed Corporation (1 page).
"We're staying ahead of the curve" Introducing the IVS Tunneller Device for Tension Free Procedures, Tyco Healthcare, 3 pages (2002).
Advantage A/T™, Surgical Mesh Sling Kit, Boston Scientific, 6 pages (2002).
Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).
Amundsen, Cindy L. et al., Anatomical Correction of Vaginal Vault Prolapse by Uterosacral Ligament Fixation in Women Who Also Require a Pubovaginal Sling; The Journal of Urology, vol. 189, pp. 1770-1774, (May 2003).
Araki, Tohru et al., The Loop-Loosening Procedure for Urination Difficulties After Stamey Suspension of the Vesical Neck, The Journal of Urology, vol. 144, pp. 319-323 (Aug. 1990).
Asmussen, M. et.al., Simultaneous Urethro-Cystometry With a New Technique, Scand J Urol Nephrol 10, p. 7-11 (1976).
Beck, Peter R. et al., Treatment of Urinary Stress Incontinence With Anterior Colporrhaphy, Obstetrics and Gynecology, vol. 59 (No. 3), pp. 269-274 (Mar. 1982).
Benderev, Theodore V., MD, A Modified Percutaneous Outpatient Bladder Neck Suspension System, Journal of Urology, vol. 152, pp. 2316-2320 (Dec. 1994).
Benderev, Theodore V., MD, Anchor Fixation and Other Modifications of Endoscopic Bladder Neck Suspension, Urology, vol. 40, No. 5, pp. 409-418 (Nov. 1992).
Bergman, Arieh et al., Three Surgical Procedures for Genuine Stress Incontinence: Five-Year Follow-Up of a Prospective Randomized Study. Am J Obstet Gynecol, vol. 173 No. 1, pp. 66-71 (Jul. 1995).
Blaivas, Jerry et al., Pubovaginal Fascial Sling for the Treatment of Complicated Stress Urinary Incontinence, The Journal of Urology, vol. 145, pp. 1214-1218 (Jun. 1991).
Blaivas, Jerry et al., Type III Stress Urinary Incontinence: Importance of Proper Diagnosis and Treatment, Surgical Forum, pp. 473-475, (1984).

(56) References Cited

OTHER PUBLICATIONS

Blaivas, Jerry, Commentary: Pubovaginal Sling Procedure, Experience with Pubovaginal Slings, pp. 93-101 (1990).
Boyles, Sarah Hamilton et al., Procedures for Urinary Incontinence in the United States, 1979-1997, Am J Obstet Gynecol, vol. 189, n. 1, pp. 70-75 (Jul. 2003).
Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294 (Feb. 1979).
Burch, John C., Urethrovaginal Fixation to Cooper's Ligament for Correction of Stress Incontinence, Cystocele, and Prolapse, Am. J. Obst. & Gyn, vol. 31, pp. 281-290 (1961).
Capio™ CL—Transvaginal Suture Capturing Device—Transvaginal Suture Fixation to Cooper's Ligament for Sling Procedures, Boston Scientific, Microvasive®, 8 pages, (2002).
Cervigni, Mauro et al., The Use of Synthetics in the Treatment of Pelvic Organ Prolapse, Voiding Dysfunction and Female Urology, vol. 11, pp. 429-435 (2001).
Choe, Jong M: et al., Gore-Tex Patch Sling: 7 Years Later, Urology, vol. 54, pp. 641-646 (1999).
Cook/Ob Gyn®, Urogynecology, Copyright Cook Urological Inc., pp. 1-36 (1996).
Dargent, D. et al., Insertion of a Suburethral Sling Through the Obturator Membrane in the Treatment of Female Urinary Incontinence, Gynecol Obstet Fertil, vol. 30, pp. 576-582 (2002).
Das, Sakti et al., Laparoscopic Colpo-Suspension, The Journal of Urology, vol. 154, pp. 1119-1121 (Sep. 1995).
Debodinance, Philipp et al., "Tolerance of Synthetic Tissues in Touch With Vaginal Scars: Review to the Point of 287 Cases", European Journal of Obstetrics & Gynecology and Reproductive Biology 87 (1999) pp. 23-30.
Decter, Ross M., Use of the Fascial Sling for Neurogenic Incontinence: Lessons Learned, The Journal of Urology, vol. 150, pp. 683-686 (Aug. 1993)
Delancey, John, MD, Structural Support of the Urethra as it Relates to Stress Urinary Incontinence: The Hammock Hypothesis, Am J Obstet Gynecol, vol. 170 No. 6, pp. 1713-1723 (Jun. 1994).
Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.
Diana, et al., Treatment of Vaginal Vault Prolapse With Abdominal Sacral Colpopexy Using Prolene Mesh, American Journal of Surgery, vol. 179, pp. 126-128, (Feb. 2000).
Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).
Enzelsberger, H. et al., Urodynamic and Radiologic Parameters Before and After Loop Surgery for Recurrent Urinary Stress Incontinence, Acta Obstet Gynecol Scand, 69, pp. 51-54 (1990).
Eriksen, Bjarne C. et al., Long-Term Effectiveness of the Burch Colposuspension in Female Urinary Stress Incontinence, Acta Obstet Gynecol Scand, 69, pp. 45-50 (1990).
Falconer, C. et al., Clinical Outcome and Changes in Connective Tissue Metabolism After Intravaginal Slingplasty in Stress Incontinence Women, International Urogynecology Journal, pp. 133-137 (1966).
Falconer, C. et al., Influence of Different Sling Materials of Connective Tissue Metabolism in Stress Urinary Incontinent Women, International Urogynecology Journal, Supp. 2, pp. S19-S23 (2001).
Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).
Farquhar, Cynthia M. et al., Hysterectomy Rates in the United States 1990-1997, Obstetrics & Gynecology, vol. 99, n. 2, pp. 229-234 (Feb. 2002).

Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6 (Dec. 1996).
Flood, C.G. et al., Anterior Colporrhaphy Reinforce With Marlex Mesh for the Treatment of Cystoceles, International Urogynecology Journal, vol. 9, pp. 200-204 (1998).
Gilja, Ivan et al., A Modified Raz Bladder Neck Suspension Operaition (Transveginal Burch), The Journal of Urology, vol. 153, pp. 1455-1457 (May 1995).
Gittes, Ruben F. et al., No-Incision Pubovaginal Suspension for Stress Incontinence, The Journal of Urology, vol. 138 (Sep. 1987)
Guner, et al., Transvaginal Sacrospinous Colpopexy for Marked Uterovaginal and Vault Prolapse, Inter J of Gybec & Obstetrics, vol. 74, pp. 165-170 (2001).
Gynecare TVT Tension-Free Support for Incontinence, The tension-free solution to female Incontinence, Gynecare Worldwide,6 pages, (2002).
Handa, Victoria L. et al, Banked Human Fascia Lata for the Suburethral Sling Procedure: A Preliminary Report, Obstetrics & Gynecology, vol. 88 No. 6, 5 pages (Dec. 1996).
Heit, Michael et al., Predicting Treatment Choice for Patients With Pelvic Organ Prolapse, Obstetrics & Gynecology, vol. 101, n. 6, pp. 1279-1284 (Jun. 2003).
Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No 1, pp. 77-82 (Mar. 1, 1978).
Hodgkinson, C. Paul et.al., Urinary Stress Incontinence in the Female, Department of Gynecology and Obstetrics, Henry Ford Hospital, vol. 10, No. 5, p. 493-499, (Nov. 1957).
Holschneider, C. H., et al., The Modified Pereyra Procedure in Recurrent Stress Urinary Incontinence: A 15-year Review, Obstetrics & Gynecology, vol. 83, No. 4, pp. 573-578 (Apr. 1994).
Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).
Ingelman-Sunberg, A. et al., Surgical Treatment of Female Urinary Stress Incontinence, Contr. Gynec. Obstet., vol. 10, pp. 51-69 (1983).
IVS Tunneller—A Universal instrument for anterior and posterior intra-vaginal tape placement, Tyco Healthcare, 4 pages (Aug. 2002).
IVS Tunneller—ein universelles instrument fur die Intra Vaginal Schlingenplastik, Tyco Healthcare, 4 pages (2001).
Jeffcoate, T.N.A. et al., The Results of the Aldridge Sling Operation for Stress Incontinence, Journal of Obstetrics and Gynaecology, pp. 36-39 (1956).
Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).
Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).
Karram, Mickey et al., Patch Procedure: Modified Transvaginal Fascia Lata Sling for Recurrent for Severe Stress Urinary Incontinence, vol. 75, pp. 461-463 (Mar. 1990).
Karram, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kersey, J., The Gauze Hammock Sling Operation in the Treatment of Stress Incontintence, British Journal of Obstetrics and Gynaecology, vol. 90, pp. 945-949 (Oct. 1983).
Klutke, Carl et al., The Anatomy of Stress Incontinence: Magentic Resonance Imaging of the Female Bladder Neck and Urethra, The Journal of Urology, vol. 143, pp. 563-566 (Mar. 1990).
Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).
Klutke, John M.D. et al, The promise of tension-free vaginal tape for female SUI, Contemporary Urology, 7 pages (Oct. 2000).

(56) References Cited

OTHER PUBLICATIONS

Korda, A, et al., Experience With Silastic Slings for Female Urinary Incontinence, Aust NZ J. Obstet Gynaecol, vol. 29, pp. 150-154 (May 1989).

Kovac, S. Robert, et al. Pubic Bone Suburethral Stabilization Sling for Recurrent Urinary incontinence, Obstetrics & Gynecology, vol. 89, No. 4, pp. 624-627 (Apr. 1997)

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).

Kovac, Stephen Robert, M.D., Cirriculum Vitae, pp. 1-33 (Jun. 18, 1999).

Leach, Gary E., et al., Female Stress Urinary Incontinence Clinical Guidelines Panel Report on Surgical Management of Female Stress Urinary Incontinence, American Urological Association, vol. 158, pp. 875-880 (Sep. 1997).

Leach, Gary E., MD, Bone Fixation Technique for Transvaginal Needle Suspension, Urology vol. XXXI, No. 5, pp. 388-390 (May 1986).

Lichtenstein, Irving L. et al, The Tension Free Hernioplasty, The American Journal of Surgery, vol. 157 pp. 188-193 (Feb. 1989).

Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).

Luber, Karl M. et al., The Demographics of Pelvic Floor Disorders; Current Observations and Future Projections, Am J Obstet Gynecol, vol. 184, n. 7, pp. 1496-1503 (Jun. 2001).

Mage, Technique Chirurgicale, L'Interpostion D'un Treillis Synthetique Dans La Cure Par Voie Vaginale Des Prolapsus Genitaux, J Gynecol Obstet Biol Reprod, vol. 28, pp. 825-829 (1999).

Marchionni, Mauro et al., True Incidence of Vaginal Vault Prolapse—Thirteen Years of Experience, Journal of Reproductive Medicine, vol. 44, n. 8, pp. 679-684 (Aug. 199).

Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).

Marshall, Victor Fray et al. The Correction of Stress Incontinence by Simple Vesicourethral Suspension, Surgery, Gynecology and Obstetrics, vol. 88, pp. 509-518 (1949).

McGuire, Edward J. et al., Pubovaginal Sling Procedure for Stress Incontinence, The Journal of Urology, vol. 119, pp. 82-84 (Jan. 1978).

McGuire, Edward J. et al., Abdominal Procedures for Stress Incontinence; Urologic Clinics of North America, pp. 285-290, vol. 12, No. 2 (May 1985).

McGuire, Edward J. et al., Experience with Pubovaginal Slings for Urinary Incontinence at the University of Michigan, Journal of Urology, vol. 138, pp. 90-93(1987).

McGuire, Edwared J. et al., Abdominal Fascial Slings, Stings, Raz Female Urology, p. 369-375 (1996).

McGuire, Edwared J., M.D., The Sling Procedure for Urinary Stress Incontinence, Profiles in Urology, pp. 3-18.

McGuire™ Suture Buide, The McGuire™ Suture Guide, a single use instrument designed for the placement of a suburethral sling, Bard, 2 pages (2001).

McIndoe, G. A. et al., The Aldridge Sling Procedure in the Treatment of Urinary Stress Incontinence, Aust. N Z Journal of Obstet Gynecology, pp. 238-239 (Aug. 1987).

McKiel, Charles F. Jr., et al, Marshall-Marchetti Procedure Modification, vol. 96, pp. 737-739 (Nov. 1966).

Migliari, Roberto et al., Tension-Free Vaginal Mesh Repair for Anterior Vaginal Wall Prolapse, Eur Urol, vol. 38, pp. 151-155 (Oct. 1999).

Migliari, Roberto et al., Treatment Results Using a Mixed Fiber Mesh in Patients With Grade IV Cystocele, Journal of Urology, vol. 161, pp. 1255-1258 (Apr. 1999).

Moir, J. Chassar et.al., The Gauze-Hammock Operation, The Journal of Obstetrics and Gynaecology of British Commonwealth, vol. 75 No. 1, pp. 1-9 (Jan. 1968)

Morgan, J. E., A Sling Operation, Using Marlex Polypropylene Mesh, for the Treatment of Recurrent Stress Incontinence, Am. J. Obst. & Gynecol, pp. 369-377 (Feb. 1970).

Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).

Morley, George W. et al., Sacrospinous Ligament Fixations for Eversion of the Vagina, Am J Obstet Gyn, vol. 158, n. 4, pp. 872-881 (Apr. 1988).

Narik, G. et.al., A Simplified Sling Operation Suitable for Routine Use, Gynecological and Obstetrical Clinic, University of Vienna, vol. 84, No. 3, p. 400-405, (Aug. 1, 1962).

Natale, F. et al., Tension Free Cystocele Repair (TCR): Long-Term Follow-Up, International Urogynecology Journal, vol. 11, supp. 1. p. S51 (Oct. 2000).

Nichols, David H., The Mersilene Mesh Gauze-Hammock for Severe Urinary Stress Incontinence, Obstetrics and Gynecology, vol. 41, pp. 88-93 (Jan. 1973).

Nicita, Giulio, A New Operation for Genitourinary Prolapse, Journal of Urology, vol. 160, pp. 741-745 (Sep. 1998).

Niknejad, Kathleen et al., Autologous and Synthetic Urethral Slings for Female Incontinence, Urol Clin N Am, vol. 29, pp. 597-611 (2002).

Norris, Jeffrey P. et al., Use of Synthetic Material in Sling Surgery: A Minimally Invasive Approach, Journal of Endourology, vol. 10, pp. 227-230 (Jun. 1996).

O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).

Ostergard, Donald R. et al., Urogynecology and Urodynamics Theory and Practice, pp. 569-579 (1996).

Paraiso et al., Laparoscopic Surgery for Enterocele, Vaginal Apex Prolapse and Rectocele, Int. Urogynecol J, vol. 10, pp. 223-229 (1999).

Parra, R. O., et al, Experience With a Simplified Technique for the Treatment of Female Stress Urinary Incontinence, British Journal of Urology, pp. 615-617 (1990).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).

Pereyra, Armand J. et al, Pubourethral Supports in Perspective; Modified Pereyra Procedure for Urinary Incontinence, Obstetrics and Gynecology, vol. 59, No. 5, pp. 643-648 (May 1982).

Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).

Peter E. Papa Petros et al., Cure of Stress Incontinence by Repair of External Anal Sphincter, Acta Obstet Gynecol Scand, vol. 69, Sup 153, p. 75 (1990).

Peter Petros et al., Anchoring the Midurethra Restores Bladder-Neck Anatomy and Continence, The Lancet, vol. 354, pp. 997-998 (Sep. 18, 1999).

Petros, Peter E. Papa et al., An Anatomical Basis for Success and Failure of Female Incontinence Surgery, Scandinavian Journal of Neurourology and Urodynamics; Sup 153, pp. 56-60 (1993).

Petros, Peter E. Papa et al., An Analysis of Rapid Pad Testing and the History for the Diagnosis of Stress Incontinence, Acta Obstet Gynecol Scand, vol. 71, pp. 529-536 (1992).

Petros, Peter E. Papa et al., An Integral Therory of Female Urinary Incontinence, Acta Obstetricia et Gynecologica Scandinavica, vol. 69 Sup. 153, pp. 7-31 (1990).

(56) References Cited

OTHER PUBLICATIONS

Petros, Peter E. Papa et al., Bladder Instability in Women: A Premature Activation of the Micturition Reflex, Scandinavian Journal of Neurourology and Urodynamics, Sup 153, pp. 235-239 (1993).
Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).
Petros, Peter E. Papa et al., Cure of Urge Incontinence by the Combined Intravaginal Sling and Tuck Operation, Acta Obstet Gynecol Scand, vol. 69, Sup 153, pp. 61-62 (1990).
Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71 (1993).
Petros, Peter E. Papa et al., Medium-Term Follow-Up of the Intravaginal Slingplasty Operation Indicates Minimal Deterioration of Urinary Continence With Time, (3 pages) (1999).
Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).
Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).
Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynarnics, Sup 153, pp. 29-40 plus cover sheet (1993).
Petros, Peter E. Papa et al., Part III: Surgical Principles Deriving From the Theory, Scandinavian Journal of Neurourology and Urodynamics, Sup 153, pp. 41-52 (1993).
Petros, Peter E. Papa et al., Part IV: Surgical Appliations of the Theory—Development of the Intravaginal Sling Pklasty (IVS) Procedure, Scandinavian Journal of Neurourology and Urodynamics, Sup 153, pp. 53-54 (1993).
Petros, Peter E. Papa et al., Pinch Test for Diagnosis of Stress Urinary Incontinence, Acta Obstet Gynecol Scand, vol. 69, Sup 153, pp. 33-35 (1990).
Petros, Peter E. Papa et al., Pregnancy Effects on the Intravaginal Sling Operation, Acta Obstet Gynecol Scand, vol. 69, Sup 153, pp. 77-79 (1990).
Petros, Peter E. Papa et al., The Autogenic Ligament Procedure: A Technique for Planned Formation of an Artifical Neo-Ligament, Acta Obstet Gynecol Scand, vol. 69, Sup 153, pp. 43-51 (1990).
Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).
Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).
Petros, Peter E. Papa et al., The Free Graft Procedure for Cure of the Tethered Vagina Syndrome, Scandinavian Journal of Neurourology and Urodynamics, Sup 153, pp. 85-87(1993).
Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, p. 73-75 (1993).
Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).
Petros, Peter E. Papa ,et al., The Intravaginal Slingplasty Operation, A Minimally Invasive Technique for Cure of Urinary Incontinence in the Female, Aust. NZ J Obstet Gynaecol, vol. 36, n. 4, pp. 453-461 (1996).
Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics, Sup 153, pp. 81-84 (1993).
Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics, Sup 153, pp. 89-93 (1993).
Petros, Peter E. Papa et al., The Role of a Lax Posterior Vaginal Fornix in the Causation of Stress and Urgency Symptoms: A Preliminary Report, Acta Obstet Gynecol. Scand, vol. 69, Sup 153, pp. 71-73 (1990).
Petros, Peter E, Papa et al., The Tethered Vagina Syndrome, Post Surgical Incontinence and I-Plasty Operation for Cure, Acta Obstet Gynecol Scand, vol. 69, Sup 153, pp. 63-67 (1990).
Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1990).
Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).
Petros, Peter E. Papa, Development of Generic Models for Ambulatory Vaginal Surgery—Preliminary Report,International Urogynecology Journal, pp. 20-27 (1998).
Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).
Petros, Peter E. Papa, Vault Prolapse II; Restoration of Dynamic Vaginal Supports by Infracoccygeal Sacropexy, An Axial Day-Case Vaginal Procedure, Int Urogynecol J, vol. 12, pp. 296-303 (2001).
Rackley, Raymond R. et al., Tension-Free Vaginal Tape and Percutaneous Vaginal Tape Sling Procedures, Techniques in Urology, vol. 7, No. 2, pp. 90-100 (2001).
Rackley, Raymond R. M.D., Synthetic Slings: Five Steps for Successful Placement, Urology Times, p. 46,48,49 (Jun. 2000).
Raz, Shlomo, et al., The Raz Bladder Neck Suspension Results in 206 Patients, The Journal of Urology, pp. 845-846 (1992).
Raz Shlomo, Female Urology, pp. 80-86, 369-398, 435-442 (1996).
Raz, Shlomo, MD, Modified Bladder Neck Suspension for Female Stress Incontinence, Urology, vol. XVII, No. 1, pp. 82-85 (Jan. 1981).
Richardson, David A. et al., Delayed Reaction to the Dacron Buttress Used in Urethropexy, The Journal of Reproductive Medicine, pp. 689-692, vol. 29, No. 9 (Sep. 1984).
Richter, K., Massive Eversion of the Vagina: Pathogenesis, Diagnosis and Therapy of the "True" Prolapse of the Vaginal Stump, Clin obstet gynecol, vol. 25, pp. 897-912 (1982).
Ridley, John H., Appraisal of the Goebell-Frangenheim-Stoeckel Sling Procedure, American Journal Obst & Gynec., vol. 95, No. 5, pp. 741-721 (Jul. 1, 1986).
Roberts, Henry, M.D., Cystourethrography in Women, Deptment of Obstetrics and Gynaecology, University of Liverpool, May 1952, vol. XXXV, No. 293, pp. 253-259.
SABRE™ Bioabsorbable Sling, Generation Now, Mentor, 4 pages (May 2002).
SABRE™ Surgical Procedure, Mentor, 6 pages (Aug. 2002).
Sanz, Luis E. et al., Modification of Abdominal Sacrocolpopexy Using a Suture Anchor System, The Journal of Reproductive Medicine, vol. 48, n. 7, pp. 496-500 (Jul. 2003).
Seim, Arnfinn et al., A Study of Female Urinary Incontinence in General Practice—Demography, Medical History, and Clinical Findings, Scand J Urol Nephrol, vol. 30, pp. 465-472 (1996).
Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).

(56) References Cited

OTHER PUBLICATIONS

Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R. et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).
Stanton, Stuart L., Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113(1986).
Staskin, David R. et al., The Gore-Tex Sling Procedure for Female Sphincteric Incontinence: Indications, Technique, and Results, World Journal of Urology, vol. 15, pp. 205-299 (1997).
Studdiford, William E., Transplantation of Abdominal Fascia for the Relief of Urinary Stress Incontinence, American Journal of Obstetrics and Gynecology, pp. 764-775 (1944).
Subak, Leslee L. et al., Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair a Ten-Year Experience, Dis. Colon Rectum, vol. 44, No. 6, pp. 857-863 (Jun. 2001).
Swift, S.E., et al., Case-Control Study of Etiologic Factors in the Development of Sever Pelvic Organ Prolapse, Int Urogynecol J, vol. 12, pp. 187-192 (2001).
TVT Tension-free Vaginal Tape, Gynecare, Ethicon, Inc., 23 pages (1999).
Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7, pp. 81-86 (May 1996).
Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol. 6, pp. 2-3 (1995).
Ulmsten, Ulf et al., A Three Year Follow Up of Tension Free Vaginal Tape for Surgical Treatment of Female Stress Urinary Incontinence, British Journal of Obstetrics and Gynaecology, vol. 106, pp. 345-350 (1999).
Ulmsten, Ulf et al., Different Biochemical Composition of Connective Tissue in Continent, Acta Obstet Gynecol Scand, pp. 455-457 (1987).
Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).
Ulmsten, Ulf et al., The Unstable Female Urethra, Am. J. Obstet. Gynecol., vol. 144 No. 1, pp. 93-97 (Sep. 1, 1982)
Vesica® Percutaneous Bladder Neck Stabilization Kit, A New Approach to Bladder Neck Suspension, Microvasive® Boston Scientific Corporation, 4 pages (1995).
Vesica® Sling Kits, Simplifying Sling Procedures, Microvasive® Boston Scientific Corporation, 4 pages (1998).
Villet, R., Reponse De R. Villet A L'Article De D. Dargent et al., Gynécolgie Obstètrique & Fertilité, vol. 31, p. 96 (2003).
Walters, Mark D., Percutaneous Suburethral Slings: State of the Art, Presented at the conference of the American Urogynecologic Society, Chicago, 29 pages (Oct. 2001).
Waxman, Steve et al., Advanced Urologic Surgery for Urinary Incontinence, The Female Patient, pp. 93-100, vol. 21 (Mar. 1996).
Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).
Webster, George et al., Voiding Dysfunction Following Cystourethropexy: Its Evaluation and Management, The Journal of Urology, vol. 144, pp. 670-673 (Sep. 1990).
Winter, Chester C., Peripubic Urethropexy for Urinary Stress Incontinence in Women, Urology, vol. XX, No. 4, pp. 408-411 (Oct. 1982).
Winters et al., Abdominal Sacral Colpopexy and Abdominal Enterocele Repair in the Management of Vaginal Vault Prolapse, Urology, vol. 56, supp. 6A, pp. 55-63 (2000).
Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).
Zacharin, Robert et al., Pulsion Enterocele: Long-Term Results of an Abdominoperineal Technique, Obstetrics & Gynecology, vol. 55 No. 2, pp. 141-148 (Feb. 1980).
Zacharin, Robert, The Suspensory Mechanism of the Female Urethra, Journal of Anatomy, vol. 97, Part 3, pp. 423-427 (1963).
Zimmern, Phillippe E. et al., Four-Corner Bladder Neck Suspension, Vaginal Surgery for the Urologist, vol. 2, No. 1, pp. 29-36 (Apr. 1994).
Mouly, Patrick et al., Vaginal Reconstruction of a Complete Vaginal Prolapse: The Trans Obturator Repair, Journal of Urology, vol. 169, p. 183 (Apr. 2003).
Pourdeyhimi, B, Porosity of Surgical Mesh Fabrics: New Technology, J. Biomed. Mater. Res.: Applied Biomaterials, vol. 23, No. A1, pp. 145-152 (1989).
Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).
Petros, Papa PE et al., An Integral Theory and its Method for the Diagnosis and Management of Female Urinary Incontinence, Scandinavian Journal of Urology and Nephrology, Supplement 153: p. 1 (1993).
Mentor Porges, Uralape, ICS/IUGA Symp, Jul. 2002.

* cited by examiner

IMPLANTS, TOOLS, AND METHODS FOR TREATMENT OF PELVIC CONDITIONS

PRIORITY CLAIM

This application is a continuation application of U.S. Ser. No. 13/432,624, filed Mar. 28, 2012, which claims priority under 35 USC §119(e) from U.S. Provisional Patent Application having Ser. No. 61/468,069, filed Mar. 28, 2011, entitled "IMPLANTS, TOOLS, AND METHODS FOR TREATMENTS OF PELVIC CONDITIONS," which applications are incorporated herein by reference in their entireties.

FIELD OF THE INVENTION

The present invention relates generally to implants, tools, devices, systems, and related methods for treating pelvic conditions including but not limited to incontinence and prolapse conditions in men and women.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

The tension of an implant (i.e., "sling") is typically adjusted during an implantation procedure in a manner to take up slack in the sling and impart desirable and efficacious tension and positioning of the implanted sling and the supported tissue. New and improved methods and devices of intra-operative adjustment of an implant are always desirable.

SUMMARY

Devices, systems, and methods as described can be applied to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), levator defects, and other conditions caused by muscle and ligament weakness, hysterectomies, and the like.

Various surgical implants, tools, and methods that relate to useful or advantageous surgical procedures are described herein. Certain embodiments of methods and implants involve an implant that includes an adjusting mechanism such as a suture (inclusive of a line, cinch, strand, suture, filament, or the like) to adjust a length of an implant (e.g., a length of an extension portion or other portion or piece of an implant), intra-operatively. Other embodiments of method and implants involve methods of placing a suture (inclusive of a suture, strand, suture, filament, or the like), at a length of an implant or an extension portion of an implant, intra-operatively, i.e., during a surgical procedure, to adjust a length of the implant or extension portion.

Described devices and methods involve pelvic implants, including surgical implants (also referred to generally herein as "slings") that include a central support portion and two or more end portions extending from the central support portion to sling ends. Herein, the terms "sling," "implant," and "incontinence sling" without further qualification are used interchangeably to include various forms of pelvic implants for supporting different pelvic tissues, and specifically include urethral slings adapted to be placed through a tissue pathway in a male or female patient, disposing the central support portion below the urethra or bladder neck (hereafter collectively referred to as the urethra for convenience) (and above the vaginal wall in a female patient) to alleviate urinary incontinence, and fecal slings adapted to be placed through a tissue pathway disposing the central support portion inferior to the anus, the anal sphincter, or the lower rectum (hereafter collectively referred to as the anus for convenience) to alleviate fecal incontinence.

In accordance with the present description, such slings can include features or be used according to methods that allow for intra-operative adjustment of the tension applied to the urethra, anus, or other supported tissue, to enhance efficacy of the implant and method of treatment and for improved patient comfort. Various specific embodiments of the implants and methods are described herein. The various embodiments are applicable to both male and female patients to address issues of incontinence in both, to address issues of prolapse repair in female patients, and to address perineal floor descent and fecal incontinence in both. Also, surgical techniques such as forming suprapubic, retropubic, transobturator, "inside-out," and "outside-in" tissue pathways between two skin incisions, or a tissue pathway formed from a single incision through the vagina or perineal floor (in male or female patients), are also contemplated for placement of a sling.

In various embodiments, sling tension or length of one or two extension portions of an implant can be adjusted by use of a suture that is located or can be placed at a location that can be accessed intra-operatively. Various sutures and tools for placing a suture, and various configurations of a suture passing through an extension portion, can be useful to decrease a length of an implant or extension portion, or to increase an amount of tension in an implant or extension portion. Optionally, an implant or method can involve the use of a suture at two opposing locations of an implant, each location being accessible through a surgical incision used to place an implant during a surgical implantation procedure. The two sutures may be used in a coordinated manner, meaning that the tension or length of both of the two opposing extension portions are adjusted together. Such coordinated adjustment can advantageously allow a surgeon or other user to adjust the placement, length, or tension of an implant in a manner that does not cause a urethra or other tissue to become located at a non-anatomical position relative to a midline of the patient. Stated differently, two opposing extension portions of an implant can be adjusted together to prevent the urethra or other supported tissue from being moved in a left or a right direction within the patient, which will maintain a correct anatomical position of the urethra or other supported tissue, e.g., at a midline of the patient.

In one aspect, the invention relates to a pelvic implant useful to treat a pelvic condition. The implant includes: a tissue support portion and two opposing extension portions, and a suture passing through an extension portion between a midline of the implant and a distal end of the extension portion. The suture is passed through the mesh such that pulling a loose end of the suture causes a length of the extension portion to decrease.

In another aspect the invention relates to a combination that includes a pelvic implant and a suture passer, the combination being useful to treat a pelvic condition. The combination includes an implant comprising a tissue support portion and two opposing mesh extension portions. The suture passer includes a proximal end, a shaft, and a shaft distal end. The shaft distal end includes a suture passer and a mesh holder. The mesh holder is capable of engaging mesh and holding the mesh between jaws of the suture passer, and the suture passer is capable of passing a suture through the mesh held between the jaws.

In another aspect the invention relates to a method of treating a pelvic condition. The method includes providing a pelvic implant useful to treat a pelvic condition, the implant including: a tissue support portion, a first extension portion and a second extension portion and a suture passing through an extension portion between a midline of the implant and a distal end of the extension portion, the suture being passed through the mesh such that pulling a loose end of the suture causes a length of the extension portion to decrease. The method also includes placing the implant in a patient to support tissue, and adjusting a length of the extension portion by tightening the suture.

In yet another aspect the invention relates to a method of treating a pelvic condition. The method includes: providing an implant that includes a tissue support portion, a first mesh extension portion, and a second mesh extension portion; providing a suture passer that includes a proximal end, a shaft, and a shall, distal end, the shaft distal end including a suture passer and a mesh holder, wherein the mesh holder is capable of engaging mesh and holding the mesh between jaws of the suture passer, and the suture passer is capable of passing a suture through the mesh held between the jaws; placing the implant in a patient to support tissue; using the suture passer to place a suture at an extension portion; and adjusting a length of the extension portion by tightening the suture.

Figure 1:
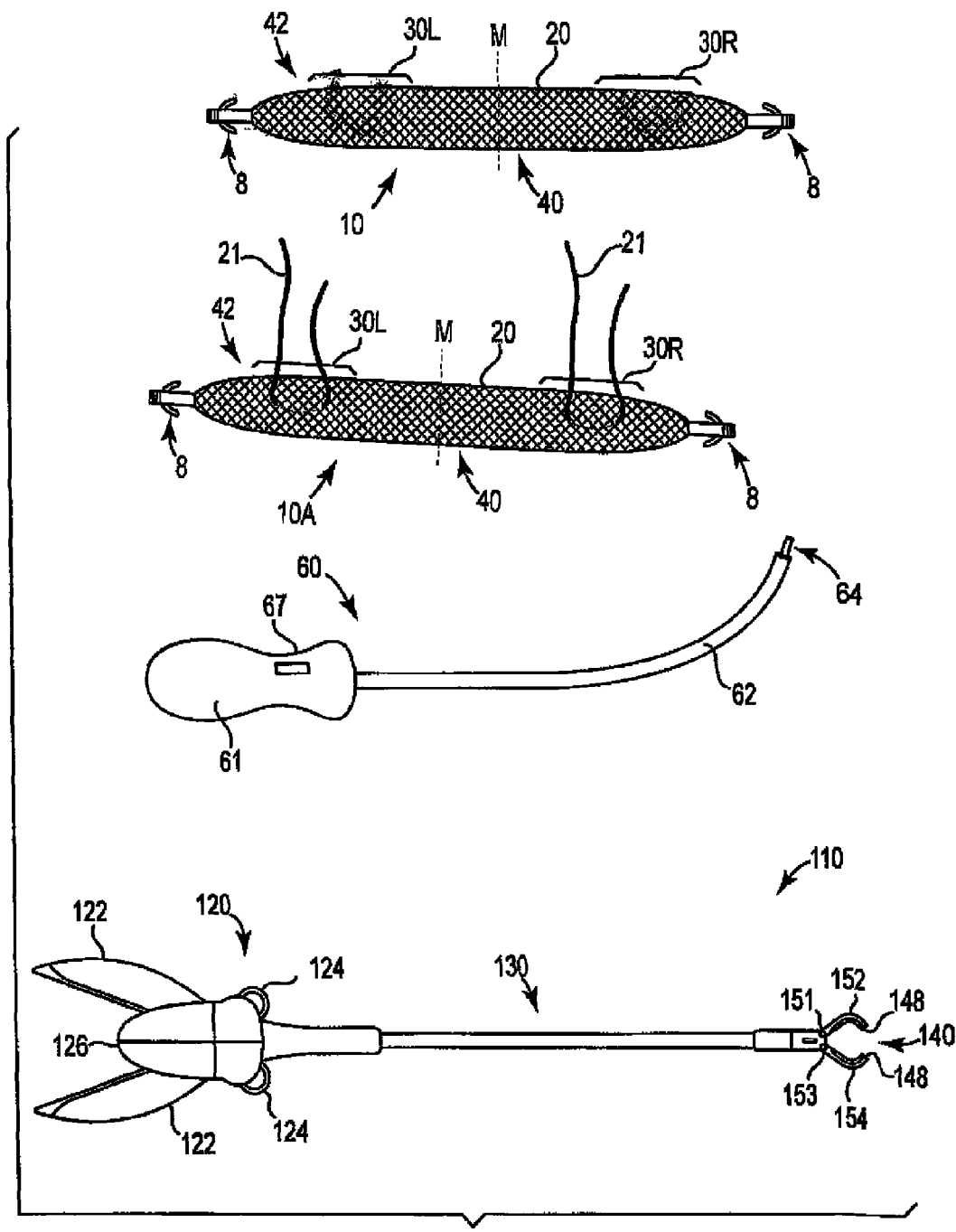
FIG. 1 shows an exemplary system or combination as described, including embodiments of implants and an optional insertion tool and optional suture passer.

All drawings are not to scale.

DETAILED DESCRIPTION

Pelvic floor disorders include urinary and fecal incontinence, prolapse, cystocele, rectocele, enterocele, uterine and vaginal vault prolapse, levator defects, and others, in male and female patients. These disorders typically result from weakness or damage to normal pelvic support systems. Common etiologies include childbearing, removal of the uterus, connective tissue defects, prolonged heavy physical labor and postmenopausal atrophy.

Vaginal vault prolapse is the distension of the vaginal apex, in some cases to an orientation outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons.

Vaginal vault prolapse is often associated with a rectocele, cystocele, or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

Sling procedures for treating urinary incontinence include surgical methods that place a supportive implant such as a sling to stabilize or support the bladder neck or urethra. Various different supportive implants and sling procedures are known. Slings and methods can differ based on the type of sling material and anchoring methods used, and placement and technique for placing and supporting the sling, including tissue to be supported. In some cases, a sling is placed under the bladder neck and secured via suspension sutures to a point of attachment (e.g. bone) through an abdominal or vaginal incision. Other techniques place a supportive portion of a sling below a urethra or bladder neck, and support the sling by placement of ends at or through obturator foramen tissue. Examples of sling procedures are disclosed in U.S. Pat. Nos. 5,112,344; 5,611,515; 5,842,478; 5,860,425; 5,899,909; 6,039,686, 6,042,534 and 6,110,101.

As used herein the terms "anchor," "tissue fastener," and "self-fixating tip," refer interchangeably and non-specifically to any structure that can connect an implant to supportive tissue of a pelvic region. The supportive tissue may preferably be a soft tissue such as a muscle, fascia, ligament, tendon, or the like. The anchor may be any known or future-developed structure useful to connect an implant to such tissue, including but not limited to a clamp, a suture, a soft tissue anchor such as a self-fixating tip, and the like.

An implant can include a tissue support portion (or "support portion") that can be used to support a urethra (including a bladder neck), bladder, vagina, levator, rectum, sphincter, or other pelvic tissue. Supporting a "urethra" refers to supporting tissue that includes the urethra (which can refer to the bladder neck), and that can optionally include tissue adjacent to a urethra such as bulbospongiosus muscle, corpus spongiosum, or both. According to specific methods involving treatment of urinary incontinence, a support portion may be placed below bulbospongiosus muscle to support both bulbospongiosus muscle and corpus spongiosum (along with the urethra), or alternately bulbospongiosus muscle may be dissected and a support portion may be placed to contact corpus spongiosum tissue (to support the urethra).

An implant can additionally include one or more extension portion (otherwise known as an "end" portion or "arm") attached or attachable to the tissue support portion. Normally for treating incontinence an implant can include two opposing extension portions. Extension portions are elongate pieces of material (e.g., mesh, molded implant material, suture, or biologic material) that extend from the tissue support portion and are connected to the tissue support portion, and are useful to attach to supportive tissue in the pelvic region (e.g., using an anchor such as a self-fixating tip or another form of tissue fastener) to thereby provide support for the tissue support portion and the supported tissue. Generally for treating incontinence, two extension portions can extend from opposite ends of a tissue support portion as elongate "ends," "arms," or "extensions," and may attach to supportive tissue in the pelvic region by extending through a tissue path to an internal anchoring point (see, e.g., Applicant's copending United States Patent Application Publication number US 2010/256442, filed Aug. 8, 2008, by Ogdahl, entitled SURGICAL ARTICLES AND METHODS FOR TREATING PELVIC CONDITIONS, the entirety of which is incorporated herein by reference), or may extend to an external incision, such as through an obturator foramen and through an external incision at a groin or inner thigh (see, e.g., Applicant's copending United States Patent Publication Number US 2006/0287571, the entirety of which is incorporated herein by reference). Also see U.S. Patent Publication number US 2011/0034759 and WO 2010/093421, PCT/US2010/057879, filed Nov. 23, 2010, and PCT/US2010/059739, filed Dec. 9, 2010, the entireties of which are incorporated hereby by reference.

In exemplary uses, each extension portion can extend from the location of attachment with the tissue support portion of the implant, through pelvic tissue, and to a location of supportive tissue within the pelvic region. The supportive tissue can be at an end of a tissue path used to perform a desired implant procedure, such as at a location near an external incision in the skin used to perform the procedure, e.g., at a location at or near an end of an extension portion placed according to a retropubic procedure or a transobturator procedure for placing a sling for treating urinary or fecal incontinence, at tissue of an obturator foramen or rectus fascia, at a ligament such as a sacrospinous ligament, etc.

An implant may include portions, pieces, or sections that are synthetic or of biologic material (e.g., porcine, cadaveric, etc.). Extension portions may be, e.g., a synthetic mesh such as a polypropylene mesh. The tissue support portion may be synthetic (e.g., a polypropylene mesh or a molded material) or biologic. Examples of implant products that may be similar to those useful according to the present description include those sold commercially by American Medical Systems, Inc., of Minnetonka Minn., under the trade names Apogee®, Perigee®, and Elevate® for use in treating pelvic prolapse (including vaginal vault prolapse, cystocele, enterocele, etc.), and Sparc®, Bioarc®, Monarc®, MiniArc®, InVance™, and AdVance™ for treating urinary incontinence.

An example of a particular type of pelvic implant is the type that includes supportive portions including or consisting of a tissue support portion and two or four extension portions extending from the tissue support portion. An implant that has exactly two or four extension portions can be of the type useful for treating urinary incontinence or vaginal prolapse. The term "supportive portions" refers to portions of an implant that function to support tissue after the implant has been implanted and specifically includes extension portions and tissue support portions, and does not include optional or appurtenant features of an implant such as a sheath, tensioning suture, tissue fastener, or self-fixating tip or other type of connector for attaching the implant to an insertion tool.

Dimensions of a tissue support portion can be any dimensions useful to support a specific tissue, e.g., urethral or vaginal tissue, for treating a pelvic condition such as incontinence, prolapse, or another pelvic condition. A tissue support portion for use in treating incontinence can be of sufficient length to support and optionally partially surround a urethra or urethra-supporting tissue. A width of a tissue support portion may optionally and preferably be greater than a width of extension portions and can be sufficiently wide to increase contact area and frictional forces between a tissue support portion and a tissue in contact with the tissue support portion. Exemplary lengths of a tissue support portion can be in the range from 0.5 to 2 inches, such as from 0.75 to 1.5 inches. Exemplary widths of a tissue support portion can be in the range from 0.4 or 0.5 to 4 centimeters, such as from 1 to 2.5 or 3 centimeters.

An implant (e.g., sling) the placement against a corpus spongiosum for treatment of urinary incontinence in a male patient may optionally and preferably include a widened central support to provide increased contact and frictional engagement with t corpus spongiosum. See, for example, Assignee's copending United States Patent Publication Number US 2006/0287571 and U.S. Pat. No. 7,422,557, the entireties of these applications being incorporated herein by reference.

Dimensions of extension portions can allow the extension portion to reach between a tissue support portion placed to support a pelvic tissue such as tissue of a urethra, vagina, anal sphincter, levator, etc, (at an end of the extension portion connected to the tissue support portion) and a location at which the distal end of the extension portion attaches to supportive tissue at or about the pelvic region. Exemplary lengths of an extension portion for use in treating incontinence by placing ends of an extension portion at tissue of an obturator foramen, for example, measured between a connection or boundary between the extension portion and the tissue support portion and a distal end of the extension portion, can be, e.g., from 0.5 to 2.5 inches, preferably from 0.5 to 1.5 inches. These or other lengths will be useful for implants designed to treat other conditions.

Implants as described can include a tissue fastener at a distal end or a distal portion of an extension portion, which is the end or portion not attached to a tissue support portion. (The term "distal" as used in this context generally refers to location at an end of an extension portion away from a tissue support portion.) A tissue fastener at a distal end or portion of an extension portion can be any of various types, including: a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Application No. PCT/US2007/014120, entitled "Surgical implants, Tools, and Methods for Treating Pelvic Conditions, filed Jun. 15, 2007; U.S. patent application Ser. No. 12/223,846, filed Aug. 8, 2008, entitled SURGICAL ARTICLES AND METHODS FOR TREATING PELVIC CONDITIONS; U.S. patent application Ser. No. 12/669,099, filed Jan. 14, 2010, entitled PELVIC FLOOR TREATMENTS AND RELATED TOOLS AND IMPLANTS; and WO 2009/075800, the entireties of which are incorporated herein by reference.) An implant may also have one or more extension portion that does not include a tissue fastener, for example if the distal end is designed to be secured to tissue by other methods (e.g., suturing), or is intended to pass through an obturator foramen and a tissue path around a pubic ramus bone, in which case the extension portion may optionally include a connector, dilator, or dilating connector, which connects to an elongate tool that can be used to either push or pull the connector, dilator, or dilating connector through a tissue path (e.g., to a medial incision).

One embodiment of a tissue fastener is a self-fixating tip. A "self-fixating tip" in general can be a structure (sometimes referred to as a soft tissue anchor) connected at a distal end of an extension portion that can be implanted into supportive tissue (e.g., muscle, fascia, ligament, or other soft tissue) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through an incision to reach the interior of the pelvic region, e.g., at a location of an obturator foramen or other supportive tissue. The insertion tool may engage the self-fixating tip at an internal channel of the self-fixating tip, at an external location such as at an external surface of the base, at a lateral extension, or otherwise as desired, e.g., in a manner to allow the insertion tool to push the self-fixating tip through an incision in a patient and through and into supportive tissue.

Exemplary self-fixating tips can include one or more lateral extensions that allow the self-fixating tip to be inserted into soft tissue and to become effectively anchored in supportive tissue. A lateral extension may be moveable or fixed. The size of the self-fixating tip and optional lateral extensions can be useful to penetrate and become anchored into the tissue. Exemplary self-fixating tips are described in Assignee's copending international patent application PCTUS2007/004015, filed Feb. 16, 2007, titled Surgical Articles and Methods for Treating Pelvic Conditions, the entirety of which is incorporated herein by reference. Other structures may also be useful.

According to exemplary embodiments, a self-fixating tip can have structure that includes a base having a proximal base end and a distal base end. The proximal base end can be connected (directly or indirectly, such as by a connective suture) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage, optionally by means of a release mechanism that can be selectively engaged and released) a distal end of an insertion tool to allow the insertion tool to be used to place the self-fixating tip at a location within pelvic tissue of the patient. A self-fixating tip can be made out of any useful material, generally including materials that can be molded or formed to a desired structure and connected to or attached to a distal end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA polylactide (PLA), copolymers of PGA and PLA.

According to various systems as described, an insertion tool may be used with implants and methods as described. Examples of useful tools include those that generally include one or more (stationary or moveable) thin elongate, relatively rigid shaft or needle that extends from a handle. The handle is located at a proximal end of the device and attaches to one end (a proximal end) of a shaft. A distal end of the shaft can be adapted to engage a portion of an implant such as a tissue fastener (e.g., a self-fixating tip), in a manner that allows the insertion tool to engage and push the tissue fastener through a tissue passage and connect the tissue fastener to supportive tissue. Examples of this type of tool can be used with a self-fixating tip that includes an internal channel designed to be engaged by a distal end of an insertion tool to allow the self-fixating tip to be pushed into tissue. Other general types of insertion tools will also be useful, but may engage a self-fixating tip or other tissue fastener in an alternate manner, e.g., that does not involve an internal channel.

Exemplary insertion tools for treatment of incontinence and vaginal prolapse are described, e.g., in U.S. patent application Ser. Nos. 10/834,943, 10/306,179; 11/347,553; 11/398,368; 10/840,646; PCT application number 2006/028828; PCT application number 20060260618; WO 2010/093421, and US Patent Publication No. 2010-0256.442 the entireties of these documents being incorporated herein by reference. These and similar tools can be used as presented in the referenced documents, or with modifications to provide features identified in the present description.

An insertion tool can optionally include a release mechanism by which a tissue fastener (e.g., a self-fixating tip) can be securely and releasable engaged with a distal end of an insertion tool such that the tissue fastener can be selectively secured to the distal end mechanically, then selectively released. With a releasable engagement, a tissue fastener (e.g., self-fixating tip) can be released from the distal end by releasing the engagement (e.g., mechanical engagement) by movement of an actuator at the proximal end of the insertion tool, such as at the handle. For example, an internal channel (or external surface) of a self-fixating tip can include an engaging surface designed to engage a mechanism at a distal end of an insertion tool shaft, while the self-fixating tip is placed at, on, or over the distal end. As an example, an internal or external surface of a self-fixating tip can include a depression, ring, edge, or ledge, that can be rounded, angular, etc. A mechanical detent such as a pin, ball, spring, lever, deflector, or other surface or extension located at the distal end of the insertion tool can be moved, deflected, or extended relative to the distal end of the insertion tool to contact the surface of the self-fixating tip to securely and releasably hold the self-fixating tip at the distal end of the insertion tool and selectively prevent removal of the tip from the distal end until removal is desired. The detent (or other surface or mechanism) can be caused to extend (or retract) from the distal end of the insertion tool by actuating a trigger or other mechanism located at the proximal end (e.g., handle or a proximal location of a shaft) of the insertion toot, to secure (or release) the self-fixating tip. Upon placement of the self-fixating tip at a desired location during a surgical implantation procedure, the insertion tool operator can release the self-fixating tip by use of the trigger or other mechanism at the handle to disengage the detent and cause the tip to become loose. The insertion tool can then be removed from the tissue path and the self-fixating tip can remain in a desired implanted location.

One exemplary form of implant useful for treatment of urinary incontinence is a "mini-sling," or "single incision sting," (e.g., as marketed by American Medical Systems under the trade name MINIARC™). Designs described herein are also useful for female pelvic floor repair products, male incontinence, for treating prolapse (e.g., vaginal prolapse), levator defects, anal incontinence, and other pelvic conditions. Devices and methods as described can be suitable for these and similar slings in the treatment of male and female urinary and fecal incontinence and to effect pelvic floor, perineal floor, and pelvic prolapse repairs that involve a variety of surgical approaches. For example, female pelvic floor repair slings may be implanted by techniques that involve transvaginal, transobturator, suprapubic, pre-pubic, or transperineal exposures or pathways. Male urinary incontinence stings may be implanted by techniques that involve transobturator, suprapubic, or transperineal pathways. Embodiments of the described devices and methods may be useful in treating fecal incontinence, by use of a transvaginal, transobturator, suprapubic or perineal floor pathway. In fecal incontinence applications, the disclosed embodiments can be used to correct the anorectal angle in the rectum to re-establish continence in patients. The above methods can, but are not necessarily limited to, use of helical needles of the type described in U.S. Pat. No. 6,911,003 or C-shaped needles or elongate needles of the type used to perform suprapubic procedures.

Referring to FIG. 1, an exemplary embodiment of an elongated sting 10 is depicted in which features of the present description may be advantageously implemented. Sling 10, including mesh 20, may be implanted by use of any of the hereindescribed manners and pathways through which at least end portions of sling 10 are drawn to dispose central support portion 40 in operative relation to a urethra, bladder neck, anal sphincter, or other supported tissue. Sling 10 includes extension portions 42 and 44, and two tissue fasteners 8 located at each of two opposing ends of the extension portions. Portions 30L and 30R are locations along lengths of extension portions 42 and 44 at which a suture may be placed (before or during a surgery) for use in reducing a length of extensions portion 42 or 44. Portions 30L and 30R are selected as locations for sutures useful to reduce lengths of extension portion 42 or 44, at least because portions 30L and 30R are locations that will be accessible through a surgical incision that is also useful to insert implant 10 into a patient, e.g., a medial (vaginal or perineal) incision. Also, portions 30L and 30R are located a desirable distance away from both midline M and self-fixating tips 8 to prevent interference of the functioning of central support portion 40 and self-fixating tips 8, when implant 10 is placed therapeutically in a patient. As exemplary locations of portions 30L and 30R, for an implant 10 useful to treat urinary incontinence in a male or female patient, ends of portions 30L and 30R may be at least 0.5 centimeter from midline M and 0.5 centimeter from a self-fixating tip 8, e.g., be at least 0.8 centimeter from midline M and 0.8 centimeter from a self-fixating tip 8.

Alternate sling 10A includes sutures 21 pre-installed at portions 30L and 30R. Sutures 21 can be placed at each of portions 30L and 30R of mesh 20, as desired, by passing through mesh 20 in two passes to form a loop, or three passes to produce a cinch in a portion 30L and 30R, or four passes to form a loop, upon tightening of suture 21, or by other useful configurations (see, e.g., FIGS. 2, 3, 4A, 4B, 4C, 4D and 4E).

Figure 2:
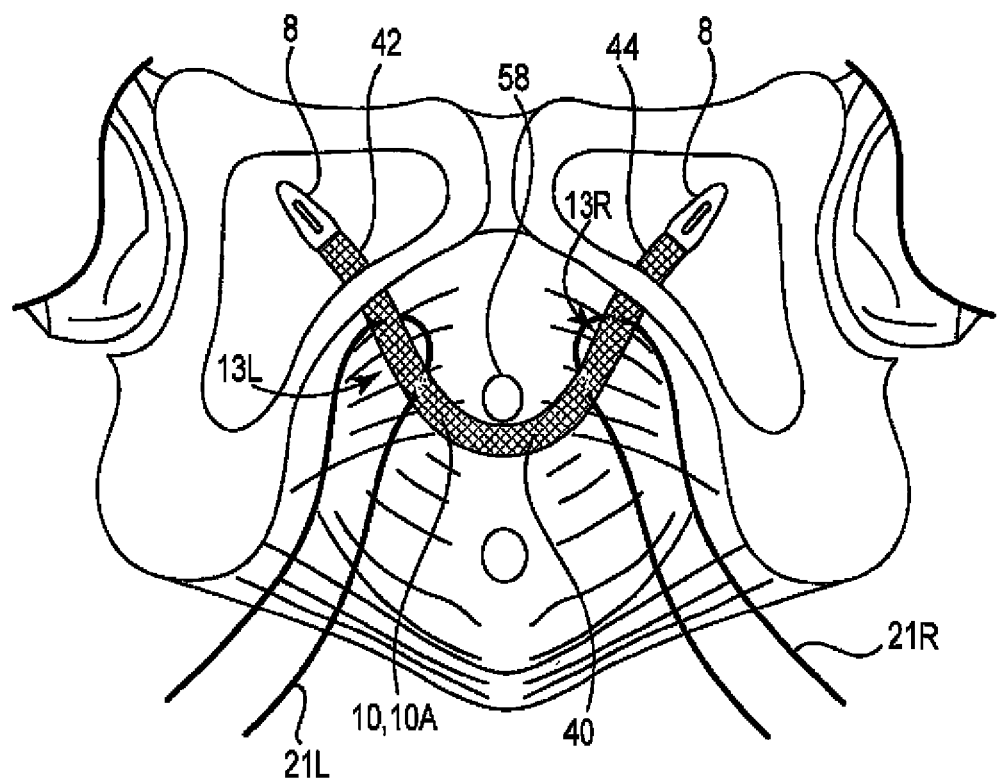
FIGS. 2 and 3 show placement of implants and selected anatomy.
Figure 3:
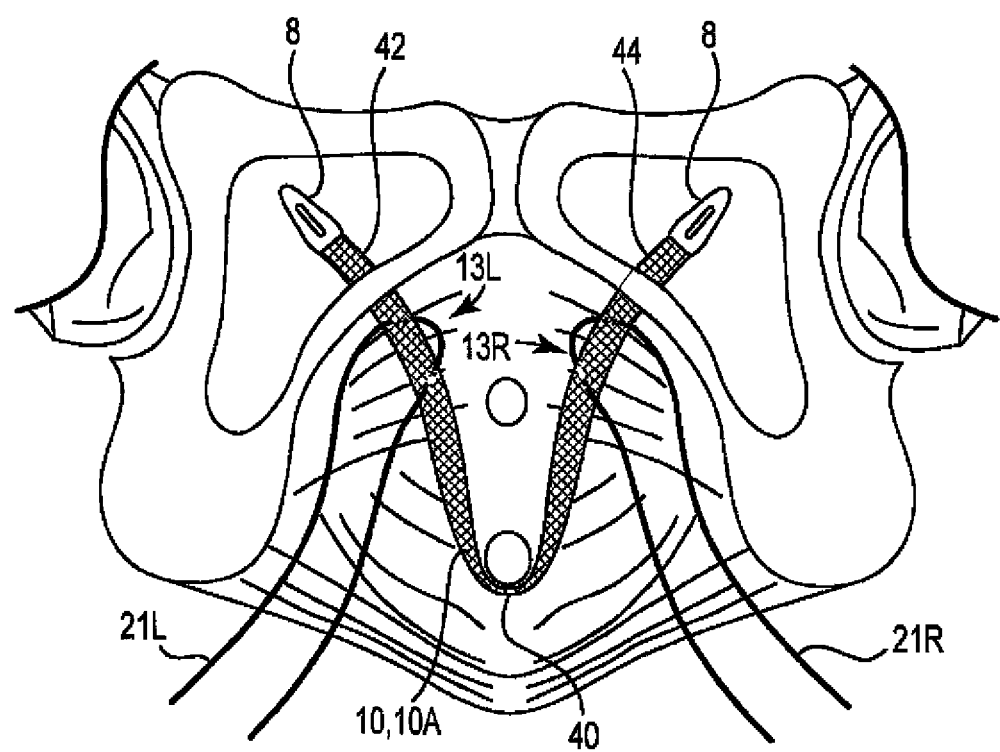

Still referring to FIG. 1, sling 10 (also herein, this refers to sling 10A) includes a first anchor (i.e., "self-fixating tip") 8, a second anchor 8, a first extension portion 42, a second extension portion 44, and a "central support portion" or "tissue support portion" 40. When designed for use in treating urinary incontinence by a single (medial) incision method, the overall dimensions of sling 10 may be 6-15 cm in length, in the range from 6 to 10, 8 to 10 centimeters in length, and 1-2 cm, more preferably 1-1.5 cm, in width (at the extension portions). For use as a single-incision sling for treating urinary incontinence, a total length dimension between opposing tissue fasteners 8 can be at least sufficient to extend from an obturator internus muscle on one side of the urethra to an obturator internus muscle on the opposite side of the urethra, with central support portion 40 placed to support tissue of a urethra. (These dimensions are for an implant designed to treat incontinence by a single incision method; dimensions can be substantially different for implants designed to treat a different conditions or for implantation by a different surgical placement method.) See FIGS. 2 and 3 showing relevant pelvic anatomy including a pelvic bone and opposed obturator foramen, implant 10, and urethra 58 and anus 67 being supported by central support portion 40.

Self-fixating tips 8 include a base, internal channel (not shown), and from two to four lateral extensions. Self-fixating tips 8, as illustrated, are designed to be inserted through a central (e.g., vaginal or perineal) incision in a patient by using insertion tool 60 (see FIG. 1), which includes handle 61 at a proximal end, shaft 62, tip 64 at a distal end of shaft 62, and optional actuator 67. Shaft 62 can be designed to extend from an external location, such as at an external medial incision at a perineum or vagina of a patient, to a location of placement of a tissue fastener, such as at an obturator foramen. Shaft 62 may be a single solid length of rigid metal or plastic. Alternately, shaft 62 may include an outer hollow sleeve and an inner (e.g., flexible) moveable shaft that can be moved, such as to actuate a release mechanism at tip 64.

Sling 10 is designed to be implanted and then left in place chronically, and includes an elongated, rectangular (as shown at FIG. 1) braided or preferably knitted, mesh strip or simply mesh 20. Sling 10 and mesh 20 are subdivided into a central support portion 40 adapted to be placed below tissue to be supported, such as a urethra. In a female patient, support portion 40 can be placed between the urethra or bladder neck and the vaginal wall. End portions 42 and 44 extend from central support portion 40 to opposing distal ends, each of which includes a tissue fastener 8 attached thereto. Mesh 20 between tissue fasteners 8 may be continuous throughout the length of sling 10. However, it will be understood that the central support portion 40 of sting 20 may be formed of other materials such that the central support portion 40 is physically attached to the end portions 42 and 44. In certain embodiments, central support portion 40 may be formed of any tissue-compatible synthetic material or any natural biocompatible material, including but not limited to treated autologous, allograft, or xenograft tissues, porcine dermis, a tissue engineered matrix, or a combination thereof. It will be understood that implant 10 may alternately be dimensioned and shaped for treatment of male or female urinary or fecal incontinence or to effect pelvic floor, perineal floor, or pelvic prolapse repairs using a variety of surgical approaches. For example, implant 10 may include more than two end portions 42 and 44 coupled to any of a connector, dilator, or tissue fastener, and extending at a variety of angles from a particularly shaped center portion 40.

In use, implant 10 (without pre-installed sutures) or 10A (with pre-installed sutures) can be initially placed with approximate positioning and effect (e.g., supportive force, approximation, or both) to support selected pelvic tissue. Subsequently, lengths of opposing extension portions 42 and 44 can be adjusted by use of one or more suture, either one or more pre-installed suture or one or more suture added intra-operatively, as described. Each self-fixating tip 8 can be placed within supportive tissue such as tissues of a patient's two opposing obturator foramen while the tissue support portion of the implant supports a urethra, bladder neck, vaginal tissue, etc.

With reference to a transvaginal method of treating urinary incontinence, as shown at FIG. 2, exemplary method steps include an initial step of placing implant 10 or 10A, followed by an adjustment step for adjusting one or two lengths of extension portions 42 and 44 by use of a suture. In a first step, self-fixating tip 8 can be placed at an end of an insertion tool 60 (optionally including a release mechanism), passed through a medial incision in a patient (e.g., transvaginally), and placed securely into tissue of an obturator foramen. The second self-fixating tip 8 located on the opposite extension portion of implant 10 can be inserted through the same medial incision and then into tissue of the opposite obturator foramen, using the same insertion tool 60 or a second identical or similar tool 60. Optionally, each step of placing a self-fixating tip at tissue of an obturator foramen can include the use of a release mechanism capable of engaging a self-fixating tip 8 at tip 64 of insertion tool shaft 62, placing the self-fixating tip 8 at supportive tissue, releasing self-fixating tip 8 from tip 64, and withdrawing insertion tool 60 from the patient.

Still referring to FIG. 2, with opposing self-fixating tips installed at opposing obturator foramen, support portion 40 is located below urethra 58, to support urethra 58. The surgeon can assess the position, tension, or both, of implant 10 or 10A, supporting urethra 58, and whether a length of extension portion 42, 44, or both, should be adjusted. If adjustment is necessary, the surgeon, will adjust by placing or tightening a suture 21 at either or both of portions 30L and 30R.

If the implant includes pre-installed sutures, 21, such as with implant 10A of FIG. 1 (see also FIGS. 2 and 3), the sutures will include loose ends 21 that extend from a front side of mesh 20 toward a surgeon and toward and optionally through the (e.g., medial) surgical incision through which implant 10 was passed to place implant 10 at the location of the patient's pelvis for supporting tissue. Using the same incision, loose ends of suture 21 can be accessed and, optionally using any useful surgical tool or instrument, can be tightened and tied or otherwise secured at the front surface of mesh 20 to reduce a length of an extension portion 42 or 44, by producing a length-reducing loop on the backside of mesh 20 (see FIG. 2C and related text), by producing a cinch in mesh 20, or by another effective use of a suture 21. If desired, a second suture 21 on the opposing side of implant 10 can be similarly tightened to reduce lengths of both opposing extension portions 42 and 44.

In preferred embodiments, using any type of pre-installed or non-pre-installed suture, two opposing sutures at portions 13L and 13R can be used in coordination to adjust lengths of opposing extension portions 42 and 44, meaning that the tension or length of both of the two opposing extension portions 42 and 44 are adjusted in a coordinated manner (e.g., simultaneously or non-simultaneously but alternately and in succession). Such coordinated use of two sutures, one at each of portion 13L and 13R, can advantageously allow the surgeon to adjust the placement, length, or tension of implant 10 in a manner that does not cause urethra 58 (or other supported tissue) to become located at a non-anatomical position relative to a midline of the patient. Stated differently, using sutures to adjust lengths at both of opposing portions 13L and 13R, together (optionally but not necessarily simultaneously using two adjusting tools), can effectively prevent urethra 58 or other supported tissue from being moved in a left or a right direction within the patient during adjustment, to maintain a correct anatomical position of the urethra or other supported tissue, e.g., at a midline of the patient.

If the implant does not include pre-installed sutures, such as is illustrated with implant 10 of FIG. 1, a suture 21 can be added to either or both of portions 30L and 30R by use of a tool or combination of tools capable of intra-operatively placing a suture at one or both of portions 30L and 30R. An example of such a tool is suture passer 110 as shown at figure it.

Referring to FIG. 1, suture passer 110 is suitable for intra-operatively passing a suture and dart assembly through an implant, such as a mesh portion 20 of implant 10. See United States Patent Publication US 2003/0023250, the entirety of which is incorporated herein by reference. Tissue passer 110 includes a proximal body portion 120, a distal jaw portion 140 including first and second opposing jaws 154 and 152, an extension portion or shaft 130 projecting distally from the portion 120, jaw manipulator (e.g. levers) 122 for opening and closing jaws 152 and 154, and a suture manipulation member 124 mounted on body portion 120 for movement relative to the body portion 120 between first and second positions to pass a suture and dart assembly from the first jaw 154 to the second jaw 152. The sizes and shapes of shaft 130 and jaws 152 and 154 are designed to allow the shaft and jaws to be passed intra-operatively through a surgical incision, such as a medial incision, to allow jaws 152 and 154 to have access to portions (e.g., 13L and 13R) of extension portions of an implant.

Suture manipulation member 124 is a manually actuated component for passing a suture 21 and dart (not shown) assembly between the jaws. Preferably, the suture manipulation member 124 comprises a pair of firing members that are positioned so that they are within easy reach of either the surgeon's thumb or index finger. Preferably, members 124 move in unison so as one pulls back on one member they both move back. Instrument 110 may conveniently be fired with either the surgeon's index finger or thumb for advancement of the dart.

Tool 110 affords an initial probe or grasp of an implant material so that a surgeon can determine an appropriate amount (length) of implant material such as mesh 20 e.g., of one of portions 30L and 30R, to include between an entry and exit of a suture, which in turn controls the size of a loop, cinch, or other collection of mesh 20 formed by tightening suture 21 after passing suture 21 through mesh 20 one or more times. The amount (length) of implant material placed between entry and exit points of a suture 21, controlled at least in part by placement of jaws 152 and 154 of tool 110, also affects the amount of adjustment (reduction) in length of an extension portion 42 or 44 that can be accomplished by partially or fully tightening the suture passing through the mesh. Specifically, in use, jaws 152 and 154 can be used to grab an amount of mesh 20 of a portion 30L and 30R, between a location of a suture entry and a suture exit. The suture may pass two, three, or four times through the mesh so that when tightened partially or completely, the suture that will produce a desired reduction in length of the mesh, and an extension portion 42 or 44. The jaw manipulating levers 122 afford a manually controlled grasping force that is independent of the actuator for passing the dart and suture assembly. The jaws 152 and 154 are operatively associated with the jaw manipulating levers 122 for movement between open and closed positions. Preferably, jaws 152 and 154 have separate pivot points 151 and 153 to provide a substantially parallel relationship between the gripping surfaces 148. Jaws 152 and 154 can be opened and closed repeatedly, as needed, allowing a surgeon to grasp and test different lengths of mesh therebetween, until a desired amount of mesh is identified for a desired degree of length reduction of an extension portion.

Figure 4A:
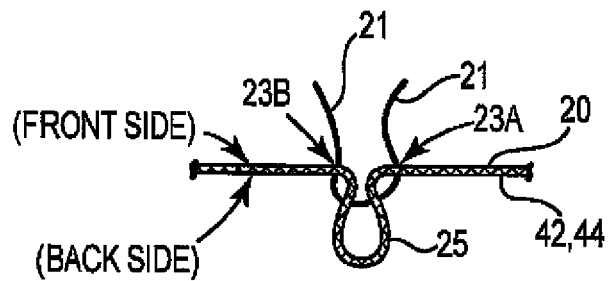
FIGS. 4A, 4B, 4C, 4D, and 4E show exemplary suture configurations.

Upon identification of a desired amount (length) of mesh to grasp between jaws 154 and 154, along with a suture entry location, suture exit location, and number of passes through mesh 20, useful to achieve a desired degree of length reduction, suture manipulation member 124 can be actuated to pass a dart and suture 21 assembly through mesh 20 of portion 30L or 30R. As illustrated at FIG. 4A, suture 21 placed at a mesh using a suture passer 110 enters a front side (toward the surgeon) of mesh 20 at first entry 23A, passes length-wise a short distance along an opposite (backside) of mesh 20, passes again through mesh 20 to exit mesh 20 at the front side, re-enters the front side a distance away to produce loop 25, passes again a short length-wise a distance along an backside of mesh 20, then passes again through mesh 20 to finally exit front side of mesh 20 at front side exit location 23B. Two loose ends of suture 21 extend from the front side of length-reduced mesh 20, and may exit a surgical incision, which as illustrated is a medial (e.g., vaginal or perineal) incision. The loose ends of suture 21 can be tightened (fully or partially) and tied or otherwise secured at the front surface of mesh 20 to produce length-reducing loop 25 on the backside of mesh 20, between first entry location 23A and final and exit location 23B of suture 21 on the front side (e.g., as illustrated at FIG. 2C). If desired, a second suture 21 can be placed at a second of the two portions 30L and 30R, on the same implant.

Optionally a tool such as suture passer 110 may include additional functionality at a distal end of shaft 130, at or near jaws 152 and 154 to assist in forming a loop, fold, or cinch in mesh 20. For example, a distal end of shaft 130 may include moveable rods or supports capable of manipulating mesh of an implant to produce a fold, loop, or cinch, in the mesh, or to gather the mesh, or to produce multiple folds or loops, by use of the an actuating mechanism at the proximal end. The distal structure can be any useful structure, such as one or more stationary or moveable arm or extensions capable of grasping and folding or looping a piece of mesh or other implant material. Upon creating of the one or more loop, fold, or cinch, etc., the loop or fold can be secured in place by passing through the mesh, as described (alternately by use of an adhesive, staple, or the like). According to this tool embodiment, the distal end of shaft 130 includes multi-functional structure capable of gathering mesh to form the one or more loop, fold, or cinch, and also securing the fold, loop, or cinch by placement of a securing device such as a suture, staple, or the like.

Figure 1A:
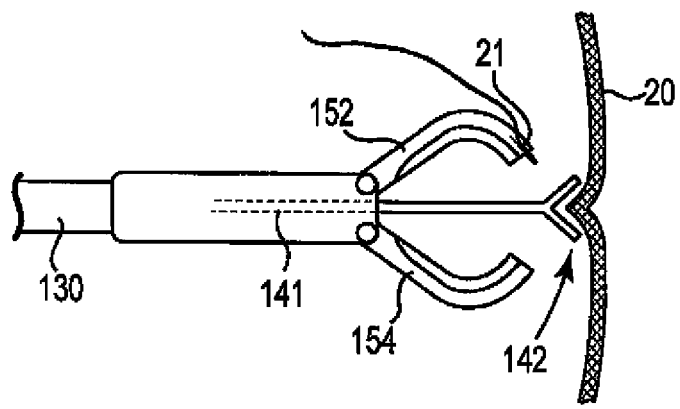
FIGS. 1A and 1B show an exemplary adjusting tool.
Figure 1B:
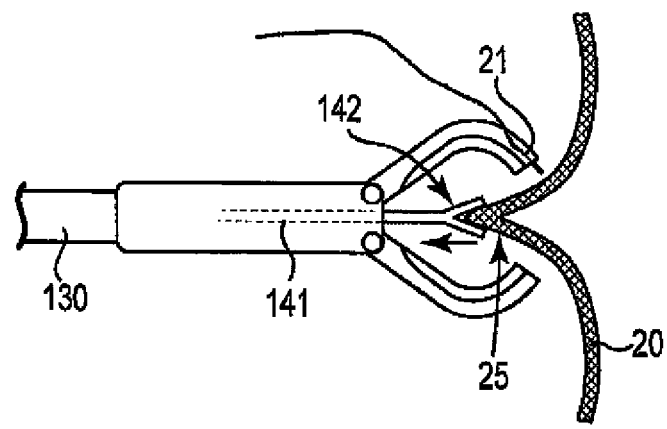

FIGS. 1A and 1B show a example of a tool that includes distal end functionality capable of manipulating implant material, e.g., mesh, to assist in passing a suture through the mesh to form a loop. As shown at FIG. 1A, shaft 130 includes a secondary shaft or other feature operative to actuate mesh-engagement feature 142, e.g., by extending and retracting mesh-engagement feature axially to and from a location beyond the reach of jaws 152 and 154, and causing mesh engagement feature 142 to engage (e.g., grasp, grip, hold) or manipulate mesh 20. In use, engagement feature 142 can be used to contact mesh 120, located beyond ends of jaws 152 and 154, grasp a location of mesh 20, and pull mesh 20 in a proximal direction within the grasp of jaws 152 and 154. With mesh 20 held within the grasp of jaws 152 and 154, jaws 152 and 154 can be closed and suture 21 can be passed through mesh 20 to form loop 25.

FIG. 2 illustrates a method of treating urinary incontinence. Implants and methods as described can also be useful to treating other pelvic conditions, such as fecal incontinence, in a similar manner. Referring to FIG. 3, a schematic illustration of a fecal incontinence sting 10 implanted in a female (for example) patient's body for treating fecal incontinence is depicted. In this illustration, central support portion 40 extends underneath the anus or anal sphincter 67 or inferior portion of the rectum (not shown, hereafter collectively referred to as the anus 67 for convenience) to correct the anorectal angle in the patient. Sutures 21L and 21R are located along lengths of extension portions 42 and 44, at portions 30L and 30R, to allow intra-operative access to, placement of, or manipulation of, each suture 21L and 21R through a medial incision in the patient. While the illustrated embodiment shows self-fixating tips 8 placed at tissue of apposing obturator foramen, other surgical approaches can be used to place sling 10 to correct fecal incontinence, including suprapubic, transobturator, retropubic, prepubic, transperineal, and transvaginal (including a single incision approach transvaginally or transperineally).

Figure 4B:
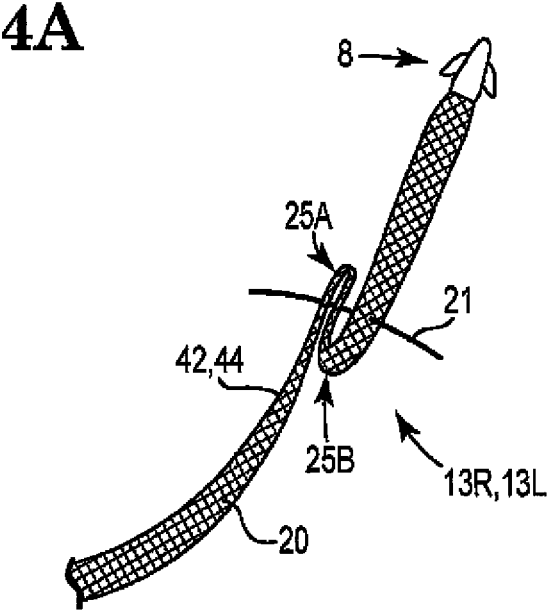

FIG. 4B shows an alternate embodiment of a path of a suture 21 through mesh 20, wherein suture 21 passes three tithes through mesh 20, to form two loops 25A and 25B.

Figure 4C:
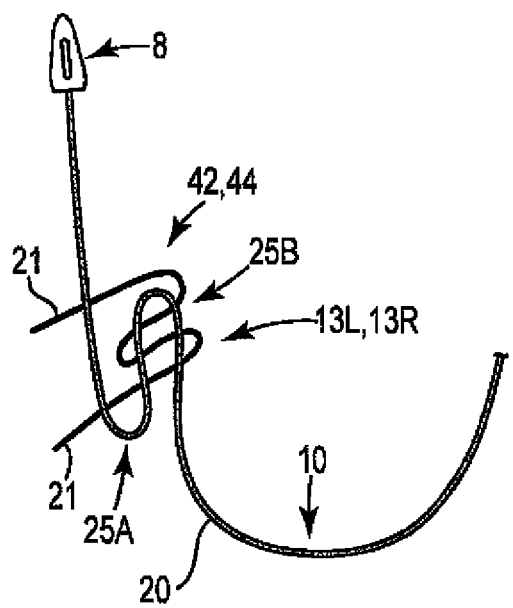

FIG. 4C shows another embodiment of a path of a suture 21 through mesh 20, wherein suture 21 passes eight times through mesh 20 to form two loops 25A and 25B.

Figure 4D:
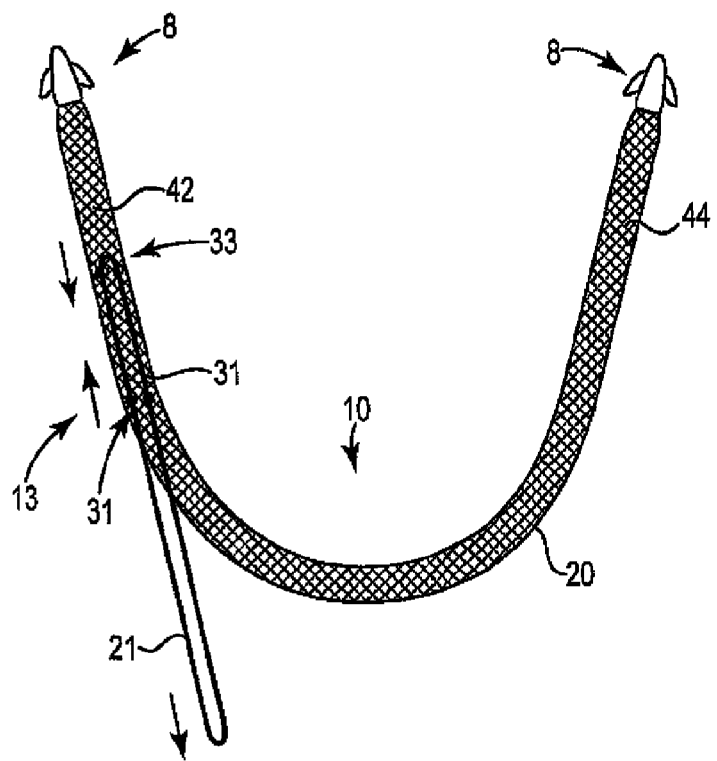

FIG. 4D shows an embodiment of a path of a suture 21 through mesh 20, wherein one suture 21 or multiple lengths of a single suture loop 21 pass along a length of mesh 20 in a side-by-side parallel configuration. Suture 21 enters mesh 20 at entry locations 31 and extends along a length of mesh 20 to attachment 33. Attachment 33 may be a knot or other secure attachment, or merely a pass of suture 21 through mesh 20. The effect is that pulling on suture 21 in a proximal direction (see proximal arrow) will cause mesh 20 to bunch or cinch together (see arrows at portion 13) between entry locations 31 and attachment 33.

Figure 4E:
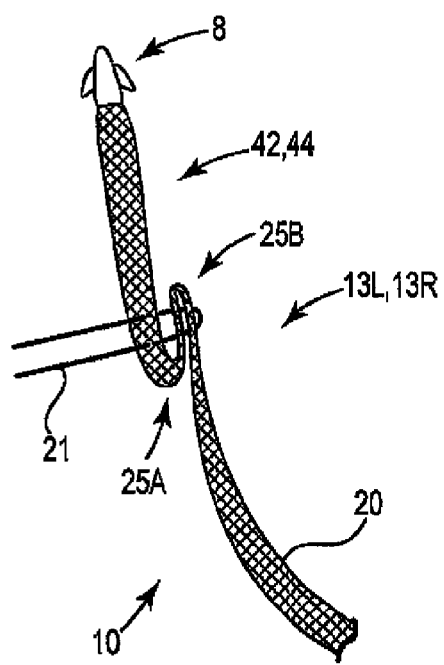

FIG. 4E shows another embodiment of a path of a suture 21 through mesh 20, wherein suture 21 passes six times through mesh 20 to form two loops 25A and 25B.

Alternately, but not illustrated, a suture may pass only once or twice through a mesh, or make any other useful number of passes. Any of the described or illustrated configurations of passing a suture 21 through a mesh 20 may be useful for either a pre-installed suture or a non-pre-installed suture, meaning a suture that is passed through the mesh before implant 10 is placed through a surgical incision and at a location to support pelvic tissue, or after implant 10 is placed through a surgical incision and at a location to support pelvic tissue, respectively. Any illustrated, described, or otherwise useful configuration can place a suture along a length of elongate mesh (e.g., an extension portion of an implant), the suture being situated within or about the mesh in a manner such that pulling the suture will cause the length of the mesh to be shortened. The embodiment at FIG. 4A, for example, includes a loop of mesh situated along the length of mesh associated with the suture. The suture enters and exits the mesh at one end of loop 25, passes along a length of the mesh, and enters and exits the mesh at a second end of loop 25. With any suture configuration, the suture can be attached or secured to the mesh (e.g., by a knot, adhesive, etc.) as necessary to result in an assembly that will cause a length of the mesh to be reduced when the suture is pulled, simultaneously creating or increasing the size of one or more loop that may be present. An implant may include a single suture on one side of an implant (e.g., FIG. 4D) or a suture on opposing sides of the implant. A suture may be pulled to a desired, complete, or partial degree, and tied or otherwise secured to effect a desired reduction in length of a mesh. And two sutures on opposed sides of an implant can be place, adjusted, tightened, and tied, in a coordinated manner, to maintain a balance between the two sides of the implant to prevent supported tissue from being pulled in a left or a right direction relative to a midline of a patient.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. A method of treating fecal incontinence, the method comprising
    providing a pelvic implant comprising
        a tissue support portion, a first extension portion, and a second extension portion, and
        a self-fixating tip at an end of each extension portion,
    providing a suture separate from the implant,
    placing the implant in a patient to support tissue selected from an anus, anal sphincter, and rectum,
    after placing the implant, placing a portion of a length of the suture through the first extension portion at two locations, each location being located between a medial end of the first extension portion and a distal end of the first extension portion, the suture being passed through the first extension portion to form at least one loop in the first extension portion such that pulling an end of the suture causes a length of the first extension portion to decrease, and
    adjusting the length of the first extension portion by pulling the suture.

2. A method as recited at claim 1 comprising providing a second suture comprising a length and a loose end, and placing a portion of the length of the second suture through the second extension portion, at two locations, each location being located between a medial end of the second extension portion and a distal end of the second extension portion, the second suture being passed through the second extension portion to form at least one loop in the second extension portion such that pulling the loose end of the second suture causes a length of the second extension portion to decrease, and adjusting the length of second extension portion by pulling the loose end of the second suture.

3. A method as recited at claim 2 comprising adjusting the length of the first extension portion and the length of the second extension portion together to prevent the supported tissue from being moved in a left or a right direction within the patient.

4. A method as recited at claim 1 comprising:
    creating a medial incision in the patient,
    placing the tissue support portion to contact tissue to support the anus,
    placing the distal end of the first extension portion in a tissue path extending toward a first obturator foramen of the patient, and
    placing the distal end of the second extension portion in a tissue path extending toward a second obturator foramen of the patient.

5. A method as recited at claim 1, comprising creating a medial incision in a pathway selected from a transvaginal, suprapubic, and perineal floor.

6. A method as recited at claim 1, comprising providing a suture passer capable of passing the suture through the first extension portion.

7. A method as recited at claim 6 comprising using the suture passer to intraoperatively place the suture through the first extension portion.

8. A method as recited as claim 6, wherein the suture passer comprises a proximal and distal end, the distal end comprising a first and a second opposing jaws capable of passing intraoperatively through a surgical incision.

9. A method as recited at claim 6, wherein passing the suture through the first extension portion creates a desired reduction in length of the implant.

10. A method as recited at claim 6, wherein the suture passer is capable of passing the suture more than one time through the first extension portion.

11. A method as recited at claim 6, wherein the suture passer comprises a proximal and distal end, the distal end comprising a mesh cincher capable of grasping the implant and a first and a second opposing jaws capable of passing the suture through the first extension portion.

12. A method as recited at claim 1, comprising creating a tissue path from a medial incision to a region selected from a bulbospongiosus muscle, an obturator foramen, or a rectus fascia tissue.

13. A method as recited at claim 1, comprising creating a tissue path from a medial incision through an obturator foramen and around a pubic ramus bone.

* * * * *